United States Patent [19]

Green et al.

[11] 3,973,563

[45] Aug. 10, 1976

[54] ADHESIVE BANDAGE BACKINGS

[75] Inventors: Percy Green, Piscataway; Margaret Cook Kordecki, Highland Park; Roger David Arnold Lipman, Princeton, all of N.J.

[73] Assignee: Johnson & Johnson, New Brunswick, N.J.

[22] Filed: Mar. 6, 1975

[21] Appl. No.: 556,029

[52] U.S. Cl. ............................... 128/156; 428/343
[51] Int. Cl.² ...................................... A61L 15/00
[58] Field of Search ..................... 128/155–157, 128/153, 165, 166; 428/310, 311, 315, 409, 343, 500, 497

[56] References Cited

UNITED STATES PATENTS

| 2,568,866 | 9/1951 | Osterhof et al. | 128/153 |
| 2,576,945 | 12/1951 | Klingel | 428/497 |
| 3,245,406 | 4/1966 | Chardack | 428/310 X |

*Primary Examiner*—Lawrence W. Trapp
*Attorney, Agent, or Firm*—Steven P. Berman

[57] ABSTRACT

Adhesive bandage backings are provided, utilizing foamed combinations of natural rubber latex and synthetic elastomeric modifying agents, that are highly conformable to irregularly shaped parts of the body and exhibit other desirable characteristics.

15 Claims, No Drawings

ADHESIVE BANDAGE BACKINGS

BACKGROUND OF THE INVENTION

Pressure sensitive adhesive bandages are used for application to various parts of the body to protect wounds from contamination, to reduce the danger of infection and to guard the wound against any further injury. These adhesive bandages usually comprise a backing, a cushion or pad, a facing, and a pressure sensitive adhesive mass coated on portions of one side of the backing. Each of these components performs a specific function in the pressure sensitive adhesive bandage and contributes to the suitability of the same for many purposes. The desirability of having adhesive bandages satisfy various objectives imposes many requirements and limitations on such bandages.

Studies have determined that during the varied daily activities of an individual, portions of the human skin normally stretch up to about 20 or 30 percent of its unstretched size and, at times, a skin stretching of about 50 percent may occur. In view of such findings, it has been determined that the ideal pressure sensitive adhesive bandage for use on the human body should have a low elastic modulus as well as high measure of elongation so that the adhesive bandage can conform to the movement of the underlying skin to which it is affixed. Thus, for example, when an adhesive bandage is applied to flexural joints such as fingers, elbows or knees, which are subjected to extensive stretching and, to a lesser degree, constriction and other distortion during normal activities, the bandage will easily stretch with the skin and substantially follow the changing contours of the skin. If the relative movement between the bandage and the skin is thus minimized, the wearer will be more comfortable and mechanical irritation will be substantially eliminated because tension on the skin will have been minimized. There will also be relatively little shifting of the adhesive bandage with respect to the skin, thereby lengthening the adhesive life of the adhesive bandage and reducing the objectionable transfer of the adhesive from the bandage to the skin. Furthermore, lengthening the adhesive life of the bandage will reduce the frequency of replacement of the bandages thereby allowing longer undisturbed healing times to the wound covered by such an adhesive bandage.

In addition to the desired elasticity and modulus properties, a desirable pressure sensitive adhesive bandage should also have a relatively high moisture vapor transmission rate in order that perspiration and other fluids on the surface of the skin may be transmitted through the bandage thereby resulting in reduced maceration of the underlying skin.

Sufficient tensile strength is another important requirement of pressure sensitive adhesive bandages in order that splitting or tearing does not occur when they are utilized. Sufficient tensile strength may not be provided merely by increasing the thickness of the bandage because thicker bandages have a tendency to roll off or peel, particularly adjacent to their edges. The problem of roll off or peel associated with such thick bandages is compounded by the surface friction of certain materials normally employed in the manufacture of adhesive bandages. For this reason, it is important that adhesive bandages be made of relatively thin materials with sufficient tensile strength to provide for the integrity of the bandage while still maintaining a low surface friction to minimize rub-off or abrasion by objects contacting the adhesive bandages in use, such as, for example, clothes.

It has been found that adhesive bandages utilizing conventional backing materials are deficient in one or more of the desired properties described above. For example, vinyl backings, such as plasticized polyvinyl chloride film or foam, have adequate strength and slip properties but lack the necessary modulus of elasticity to give good conformability to the bandages, especially when these bandages are applied to flexural joints, such as fingers, elbows or knee joints. On the other hand, polyurethane foams, which have been also suggested for use as adhesive bandage backings, provide good conformability, but have relatively high surface friction and low tensile strength. Styrene-butadiene rubber foams have also been tried as backing materials in the prior art without much success due to their insufficient strength. Natural rubber latex foams have excellent conformability characteristics and high strength, however, they present the disadvantage of having a high friction surface.

It is to these prior-art problems of limited elasticity and conformability and poor splitting and tear resistance, coupled with high surface friction, that the present invention is specifically directed, although the adhesive bandage backings of the present invention also excel in meeting the various other requirements for a high quality adhesive bandage, including the important requirement of "breathability."

It is therefore a general object of the present invention to provide a pressure sensitive adhesive bandage backing which meets the desired requirements for such a product. It is a more specific object to provide an adhesive bandage backing which is conformable to irregularly-shaped body portions and sufficiently thin to minimize peeling as a result of friction and contact with other objects. It is still another object to provide a pressure sensitive adhesive bandage backing which will conform to the various parts of the body regardless of the normal movement or change in shape thereof. These and other objects of the present invention will become more apparent from the description hereinafter.

SUMMARY OF THE INVENTION

It has now been discovered that adhesive bandage backings made from specific blends of a natural rubber latex and one or more synthetic elastomeric modifying agents possess the above discussed desired qualities.

According to the present invention, the adhesive bandage backings are made of specific blends of a natural rubber latex in combination with at least one synthetic elastomeric modifying agent selected from the group consisting of styrene-butadiene rubber (SBR), polyurethane, plasticized polyvinyl chloride, neoprene rubber, nitrile rubber, and ethylene vinyl chloride copolymers. Proportions of these components may vary according to the requirements of the specific end products but in order to achieve the desired results of the present invention, at least 45 parts by weight of the natural rubber and at least 10 parts by weight of the elastomeric modifying agents are necessary in the adhesive bandage backings. The natural rubber can be present from about 45 to 90 parts by weight and the elastomeric modifying agent can be present from about 10 to 55 parts by weight.

The term "natural rubber" as used in describing this invention includes both the naturally occuring form of rubber, i.e., cis-1,4-polyisoprene, as well as synthetically prepared cis-1,4-polyisoprene. The term "elastomeric modifying agent" as used in describing this invention includes the normally rubbery materials as well as the elastoplastic materials such as plasticized polyvinyl chloride and when the term is utilized or when the specific elastomeric modifying agents are disclosed, it is understood that these agents are initially in latex form when blended with the natural rubber latex to form the desired adhesive bandage backings.

DETAILED DESCRIPTION OF THE INVENTION

The blends of natural rubber and elastomeric modifying agents which comprise the adhesive bandage backings of the present invention can be exemplified by the following sample blends:

| Blend | Range for Natural Rubber (Parts by Weight) | Range for Elastomeric Modifying Agent (Parts by Weight) |
| --- | --- | --- |
| Natural Rubber/SBR | 50–90 | 10–50 |
| Natural Rubber/Polyurethane | 50–80 | 20–50 |
| Natural Rubber/Plasticized Polyvinyl Chloride/SBR | 45–75 | 20–50; 0–20 |
| Natural Rubber/Neoprene | 50–90 | 10–50 |
| Natural Rubber/Ethylene Vinyl Chloride Copolymer | 50–90 | 10–50 |

It has been observed that an increase in the natural rubber latex content in a blend results in increased elasticity, tensile strength, and tear resistance. It has further been observed that an increase in the polyurethane content in a blend results in a higher modulus and an increase in the plasticized polyvinyl chloride content in a blend results in a smoother surface and less friction.

The blends of natural rubber latex and elastomeric modifying agents which form the adhesive bandage backing compositions are prepared in foam form. Generally, these foams are prepared by charging specific quantities of ingredients into a stirring vessel. These ingredients and their general order of addition are: natural rubber latex; a wetting or foaming agent such as the soaps and detergents known for such qualities, for example, the alkali metal stearates and oleates such as potassium oleate; an alkaline pH control agent, such as potassium hydroxide, to maintain a pH of at least 10 for stability purposes; the synthetic elastomeric modifying agents; a "cure mix" and a suitable coloring agent. If desired, silicone oils such as those sold under the trademark Dow Corning DC-200 can also be added to aid in reducing friction.

The resulting mixture is stirred until all the ingredients are thoroughly dispersed and then the mixture is foamed according to conventional foaming techniques in a suitable foamer, such as the Oakes Foamer, (manufactured by E. T. Oakes Corp., Islip, N.Y.). The resulting foam is then pumped into a suitable blender, such as the Oakes Blender, (manufactured by E. T. Oakes Corp.), where metered quantities of a cure activator such as zinc oxide and, if necessary, a suitable gelling agent such as ammonium acetate, are mixed with the foam. After a sufficient blending time has elapsed, the foam can be coated onto specially prepared carrier paper by means of a reverse roll coater and cured in a succession of ovens. The temperature of the oven zones may vary from 200°F to 375°F, depending on the formulation, its thickness and the speed of the conveyor carrying the product through the oven zones.

The cure mix may contain accelerators to speed up the reaction, sulfur which functions as a cross-linking agent, antioxidants to prevent discoloration and weakening of the resulting product and if required, gelling agents. Gelling agents can also be added at the time the cure activator is added.

Typical accelerators which may be utilized in the cure mix to form the compositions of the present invention are, for example, dimethylethyl thiourea, 1,3-dibutyl thiourea, bismuth dimethyldithiocarbamate, copper dimethyldithiocarbamate, selenium diethyldithiocarbamate, tellurium diethyldithiocarbamate, potassium di-n-butyl dithiocarbamate, sodium di-n-butyldithiocarbamate, activated dithiocarbamate, zinc diethyldithiocarbamate, zinc diemthyldithiocarbamate, zinc di-n-butyldithiocarbamate, 4-morpholinyl-2-benzothiazyl disulfide, zinc isopropyl xanthate, dipentamethylene thiuram hexasulfide, tetramethylthiuram monosulfide, tetramethylthiuram disulfide, tetraethylthiuram disulfide, zinc 2-mercaptobenzothiazole, n-oxydiethylene benzothiazole-2-sulfenamide, 2-mercaptobenzothiazole, benzothiazyl disulfide, and the like. The accelerators are employed in amounts ranging from about 0.25 to 10 parts per hundred parts of latex.

Typical antioxidants which may be utilized in the cure mix to form the compositions of the present invention are, for example, alkylated diphenylamines, diphenyl-p-phenylene-diamine, p-isopropoxy diphenylamine, phenyl-β-napthylamine, di-β-napthyl-p-phenylenediamine, polymerized 1,2-dihydro-2,2,4-trimethylquinoline, polybutylated bisphenol-A, trifunctional hindered phenolics, styrenated phenols, hindered alkylated polymeric bisphenols, and the like. Generally, from about 1 to about 3 parts of antioxidant per hundred parts of latex are employed.

The gelling agents which may be utilized in the cure mix, if required, include ammonium acetate, ammonium sulfate, sodium silicofluoride, potassium silicofluoride, quaternary amines, cationic soaps and detergents, diphenyl guanidine, and the reaction product of ethyl chloride, formaldehyde, ammonia sold under the trade name "TRIMENE BASE" and the like. The gelling agents are employed in amounts of from about 0.01 to about 3 parts per hundred parts of latex.

Other additives may be employed if desired, for example, dyes and pigments which can be admixed as a coloring agent with the latex compositions to impart color thereto, deodorants which can be added to the latex compositions to mask the sometimes unpleasant rubber odor; and the like. Such additives and other components such as the cure activators, the pH control agents, the foaming agents and the silicone oils employed in the latex formulations of the present invention may be present in the range of from about 2 parts to about 15 parts per hundred parts of the latex.

The adhesive bandage backings of the present invention may be incorporated into various pressure sensitive adhesive bandages, such as finger, elbow, knee, spot and the like bandages. The adhesive which is coated to portions of the backing may be any conventional porus pressure sensitive adhesive used in the preparation of such adhesive bandages, surgical dressings and the like, the particular type per se not being part of the present invention. Suitable adhesives are, for example, the rubber based adhesives and the acrylate pressure-sensitive adhesives presently used in adhesive bandage constructions, see, for example, U.S. Pat. No. 2,884,126 (U.S. Pat. Re. No. 24,906) which discloses a pure rubbery copolymer of isoctyl acrylate and acrylic acid in a 94:6 ratio. Other adhesives such as the polyvinyl ether adhesives can also be utilized. The amount of adhesive depends upon the particular adhesive, the end use of the product and the like. The adhesive may be applied to the backings by conventional techniques. Such adhesive bandages should also contain an absorbent pad positioned on a part of the adhesive coating leaving said adhesive surface uncovered in some portions. The pad can be composed of any well-known material suitable for such use.

Specific embodiments of the adhesive bandage backing compositions, prepared in accordance with the present invention are illustrated by the following representative examples. It will be understood, however, that the invention is not confined to the specific limitations set forth in the individual examples, but rather to the scope of the appended claims.

EXAMPLE I

An adhesive bandage backing composition containing 80 parts natural rubber and 20 parts styrene-butadiene rubber (SBR) is prepared by placing metered quantities of the ingredients listed below except the zinc oxide and the ammonium acetate into a vessel at room temperature. The vessel is then stirred until all the ingredients are thoroughly dispersed and thereafter the mixture is foamed in a suitable foamer. The foam is then pumped into a suitable blender where metered quantities of zinc oxide and ammonium acetate are mixed with the foam. After sufficient blending time the foam is coated onto a carrier paper by means of a reverse roll coater manufactured by Ross Engineering, Highland Park, New Jersey, and cured in a succession of ovens at a temperature of about 240°C.

| Ingredients in Order of Addition | Parts, Dry | Parts, Wet |
| --- | --- | --- |
| Natural Rubber Latex | 80 | 116 |
| Potassium Oleate | 1.2 | 6 |
| SBR Latex | 20 | 28 |
| Potassium Hydroxide | 0.2 | 2 |
| Cure Mix (sulfur, zinc di-n-dibutyldithiocarbamate, zinc 2-mercaptobenzothiazole and di-β-napthyl-p-phenylenediamine) | 6 | 10 |
| Coloring Agent | 0.5 | 1 |
| Zinc Oxide | 2.4 | 4 |
| Ammonium Acetate | 0.2 | 2 |

EXAMPLE II

An adhesive bandage backing composition containing 65 parts natural rubber, 30 parts plasticized polyvinyl chloride and 5 parts styrene-butadiene rubber (SBR) consisting of the following ingredients is prepared in accordance with the procedure of Example I:

| Ingredients in Order of Addition | Parts, Dry | Parts, Wet |
| --- | --- | --- |
| Natural Rubber Latex | 65 | 94 |
| Potassium Oleate | 1.2 | 6 |
| Plasticized Polyvinyl Chloride Latex | 30 | 57 |
| SBR Latex | 5 | 7 |
| Potassium Hydroxide | 0.2 | 2 |
| Cure Mix (sulfur, zinc diethyldithiocarbamate, zinc mercaptobenzothiazole and hindered alkylated polymeric bisphenol) | 6 | 10 |
| Coloring Agent | 0.05 | 1 |
| Zinc Oxide | 2.4 | 4 |
| Ammonium Acetate | 0.2 | 2 |

EXAMPLE III

An adhesive bandage backing composition containing 65 parts natural rubber and 35 parts polyurethane consisting of the following ingredients is prepared in accordance with the procedure of Example I:

| Ingredients in Order of Addition | Parts, Dry | Parts, Wet |
| --- | --- | --- |
| Natural Rubber Latex | 65 | 94 |
| Potassium Oleate | 1.2 | 6 |
| Polyurethane Latex | 35 | 68 |
| Potassium Hydroxide | 0.2 | 2 |
| Cure Mix (sulfur, zinc diethyldithiocarbamate, zinc mercaptobenzothiazole and hindered alkylated polymeric bisphenol) | 6 | 10 |
| Coloring Agent | 0.5 | 1 |
| Silicone Oil | 2.0 | 2 |
| Zinc Oxide | 2.4 | 4 |
| Ammonium Acetate | 0.2 | 2 |

EXAMPLE IV

An adhesive bandage backing composition containing 65 parts natural rubber and 35 parts ethylene vinyl chloride copolymer consisting of the following ingredients is prepared in accordance with the procedure of Example I:

| Ingredients in Order of Addition | Parts, Dry | Parts, Wet |
| --- | --- | --- |
| Natural Rubber Latex | 65 | 94 |
| Potassium Oleate | 1.2 | 6 |

-continued

| Ingredients in Order of Addition | Parts, Dry | Parts, Wet |
|---|---|---|
| Ethylene Vinyl Chloride Copolymer Latex | 35 | 74 |
| Potassium Hydroxide | 0.2 | 2 |
| Cure Mix (sulfur, zinc diethyldithiocarbamate, zinc mercaptobenzothiazole and hindered alkylated polymeric bisphenol) | 6 | 10 |
| Silicone Oil | 2 | 2 |
| Coloring Agent | 1 | 2 |
| Zinc Oxide | 2.4 | 4 |
| Ammonium Acetate | 0.2 | 2 |

EXAMPLE V

An adhesive bandage backing composition containing 75 parts natural rubber and 25 parts neoprene rubber consisting of the following ingredients is prepared in accordance with the procedure of Example I:

| Ingredients in Order of Addition | Parts, Dry | Parts, Wet |
|---|---|---|
| Natural Rubber Latex | 75 | 120 |
| Potassium Oleate | 1.2 | 6 |
| Miranol L2MSF. Conc. | 0.1 | 1 |
| Neoprene Rubber Latex | 25 | 42 |
| Cure Mix (sulfur, zinc diethyldithiocarbamate, zinc mercaptobenzothiazole and hindered alkylated polymeric bisphenol) | 6 | 11 |
| Zinc Oxide | 6 | 10 |

As discussed above, conventional adhesive bandage backings have been deficient in one or more of the desired properties of such bandages, for example, elasticity and modulus properties, sufficient tensile strength, adequate moisture vapor transmission rate and low surface friction.

A tensile strength of from about 75 to 500 pounds per square inch (psi) and preferably of from about 150 to 500 psi for certain special bandages, for example, finger bandages, is desired. A percent elongation at break of from about 10 to 500 and preferably of from about 100 to 500 is desired and a 100 percent modulus of about 15 to 100 pounds per square inch, and preferably from about 40 to 100 psi for finger bandages and preferably about 15 to 60 psi for elbow or knee bandages is desired. A thickness of from about 5 to 27 mils depending on the end product use, and preferably of from about 10 to 25 mils and an Elmendorf Tear of from about 1 to 16 grams and preferably from about 4 to 16 grams is also desired. Still further, a surface friction measured by angle of slip of from about 1 to 60; and a moisture vapor transmission rate of at least 0.08 gms/cm$^2$/24 hrs is desirable.

Tensile stength is defined as the force, expressed in pounds per inch-width of the sample, required to break the sample. It is determined, using a suitable instrument, by clamping a 1-inch wide and 4-inch long strip of a sample with the clamps of the instrument being exactly 2 inches apart and exerting a steady 10-inch per minute pull on the sample. The force required to break the sample is recorded as the tensile strength of the sample.

Elongation or extent of elasticity means extensibility to breaking point of a sample beyond its relaxed length expressed in percent. The determination of elongation at break is similar to that of tensile stength. A 1-inch by 4-inch sample is held by the clamps of an instrument so that the gap length between the clamps is exactly 2 inches. A pulling force is applied on the sample until a break occurs in the sample. The length of the sample at break divided by its original, relaxed length (2 inches) and multiplied by 100 give percent elongation at break.

One hundred per cent modulus expressed in psi, is defined as the slope of the tangent drawn to the stress-strain curve at a 2-inch elongation divided by the sample thickness. Surface friction, expressed as angle of slip in degrees, is measured by a suitable instrument, such as a McLaughlin Tilting Platform Tester, manufactured by Precision Machine and Development Company, New Castle, Del. The platform is set at an angle of inclination of zero degrees from the horizontal. A sample of size 2 inches × 1⅜ inches is anchored to the platform. A sliding card of 2 inches × 1⅜ inches covered with a woven cotton cloth having a total weight of 1.425 grams is laid on top of the sample. The platform is slowly tilted until the card slips off. The angle of inclination at slip is recorded. Moisture vapor transmission rate is the weight of water lost by evaporation through a sample at 100°F. over a period of 24 hours.

Various foams were prepared comprising 100 percent natural rubber, 100 percent SBR, 100 percent polyurethane and 100 percent plasticized polyvinyl chloride in accordance with the procedure of Example I. The physical characteristics of these foams were measured in accordance with the above-described methods and the results are reported in Table I below.

TABLE I

Physical Characteristics of Foams Containing Only One Type of Latex

| Description | Thickness (mils) | Tensile* (psi) | 100% Modulus (psi) | Elongation* at Break (%) | Surface Friction (° slip) | Moisture Vapor Transmission (gm/cm$^2$/ 24 hrs.) | Elmendorf Tear (grams) | Density (lbs/ft$^3$) |
|---|---|---|---|---|---|---|---|---|
| 100% SBR | 55 | 16.8 | 5.7** | 104 | 90° | .490 | 1.84 | 10 |
| 100% Natural Rubber | 20 | 377 | 12.1* | 797 | 90° | .32 | 11.9 | 22 |
| 100% Polyurethane | 48 | 214 | 46.9** | 84 | 75° | .10 | 3.2 | 25 |
| 100% Plasticized Polyvinyl Chloride | 55 | 87.5 | N/A*** | 28 | 54° | .21 | 1.6 | 10 |

*Average of values for cross direction and machine direction.
**Machine direction only. Did not reach 100% elongation in cross direction.
***Did not reach 100% elongation in either direction.

As can readily be seen from Table I, the foams containing a single latex ingredient were each deficient in one of the desired characteristics. For example, the 100 percent SBR and 100 percent natural rubber each had high surface friction and the 100 percent polyurethane and 100 percent plasticized polyvinyl chloride each lacked the desired modulus of elasticity. Other undesired characteristics are also shown in the results in Table I.

The physical characteristics of the compositions of the present invention (Examples I–V) were also measured in accordance with the above-described methods and the results are reported in Table II below.

TABLE II

Physical Characteristics of Foams Containing Latex Blends

| Description | Thickness (mils) | Tensile* (psi) | 100% Modulus (psi) | Elongation* at Break (%) | Surface Friction (° slip) | Moisture Vapor Transmission (gm/cm²/ 24 hrs.) | Elmendorf Tear (grams) | Density (lbs/ft³) |
|---|---|---|---|---|---|---|---|---|
| 80 Natural Rubber/20 SBR | 10 | 213 | 9 | 516 | 79° | 0.80 | 1.1 | 19 |
| 65 Natural Rubber/30 Plasticized Polyvinyl Chloride/5 SBR | 12 | 141 | 17 | 147 | 45° | 0.13 | 1.5 | 19 |
| 65 Natural Rubber/ 35 Polyurethane | 11 | 262 | 37 | 121 | 51° | 0.15 | 1.4 | 25 |
| 65 Natural Rubber/35 Ethylene Vinyl Chloride Copolymer | 13 | 175 | 13 | 345 | 51° | 0.12 | N/A | 13 |
| 75 Natural Rubber/25 Neoprene | 6 | 221 | 28 | 691 | 60° | 0.19 | 1.0 | 18 |

*Average of values for cross direction and machine direction.

As shown in Table II, the combination foams possess the characteristics desired for adhesive bandage backings. They possess the property of high elongation along with low elastic modulus so that the adhesive bandage will conform to the movement of the underlying skin to which it is attached. They possess sufficient tensile strength without being thick and bulky along with low surface friction to minimize rub-off or abrasion by objects contacting the bandage. They are also moisture vapor transmittant to minimize maceration of skin, itching and discomfort to the user.

Various other features and embodiments of the present invention not specifically enumerated will be obvious to those skilled in the art, all of which may be achieved without departing from the spirit and the scope of the invention as defined by the following claims.

What is claimed is:

1. A highly conformable pressure-sensitive adhesive bandage backing comprising at least 45 parts by weight of natural rubber and at least 10 parts by weight of at least one synthetic elastomeric modifying agent selected from the group consisting of styrene-butadiene rubber, polyurethane, plasticized polyvinyl chloride, neoprene rubber, nitrile rubber, ethylene vinyl chloride copolymer, and mixtures thereof; wherein said backing has a tensile strength of from about 75 to 500 pounds per square inch.

2. The adhesive bandage backing of claim 1, wherein the elastomeric modifying agent is styrene-butadiene rubber.

3. The adhesive bandage backing of claim 1, wherein the elastomeric modifying agent is polyurethane.

4. The adhesive bandage backing of claim 1, wherein the elastomeric modifying agent is plasticized polyvinyl chloride.

5. The adhesive bandage backing of claim 1, wherein the elastomeric modifying agent is neoprene rubber.

6. The adhesive bandage backing of claim 1, wherein the elastomeric modifying agent is nitrile rubber.

7. The adhesive bandage backing of claim 1, wherein the elastomeric modifying agent is ethylene vinyl chloride copolymer.

8. The adhesive bandage backing of claim 1, wherein the elastomeric modifying agent is a mixture of plasticized polyvinyl chloride and styrene-butadiene rubber.

9. The adhesive bandage backing of claim 1, said backing having a percent elongation at break of from about 10 to 500.

10. The adhesive bandage backing of claim 1, said backing having a 100 percent modulus of about 15 to 100 pounds per square inch.

11. The adhesive bandage backing of claim 1, said backing having a thickness of from about 5 to 27 mils.

12. The adhesive bandage backing of claim 1, said backing having a surface friction measured by angle of slip of from about 1 to 60.

13. The adhesive bandage backing of claim 1, said backing having a moisture vapor transmission rate of at least about 0.08 gms/cm²/24 hrs.

14. A highly conformable pressure-sensitive adhesive bandage backing comprising about 45 to 90 parts by weight of natural rubber and about 10 to 55 parts by weight of at least one synthetic elastomeric modifying agent selected from the group consisting of styrene-butadiene rubber, polyurethane, plasticized polyvinyl chloride, neoprene rubber, nitrile rubber, and ethylene vinyl chloride copolymer; said backing having
 a tensile strength of from about 75 to 500 pounds per square inch;
 a percent elongation at break of from about 10 to 500;
 a 100 % modulus of about 15 to 100 pounds per square inch;
 a thickness of from about 5 to 27 mils;
 a surface friction measured by angle of slip of from about 1 to 60; and
 a moisture vapor transmission rate of at least 0.08 gms/cm²/24 hrs.

15. A pressure-sensitive adhesive bandage comprising a backing having a coating of a pressure-sensitive adhesive on one side thereof, an absorbent pad positioned on said adhesive surface and leaving said adhesive surface uncovered in some portions, said backing comprising at least 45 parts by weight of natural rubber and at least 10 parts by weight of at least one synthetic elastomeric modifying agent selected from the group consisting of styrene-butadiene rubber, polyurethane, plasticized polyvinyl chloride, neoprene rubber, nitrile rubber, and ethylene vinyl chloride copolymers and mixtures thereof, wherein said backing has a tensile strength of from about 75 to 500 pounds per square inch.

* * * * *